(12) United States Patent
Ramakrishnan

(10) Patent No.: US 7,192,732 B2
(45) Date of Patent: Mar. 20, 2007

(54) REGULATION OF HUMAN CASPASE-1-LIKE PROTEASE

(75) Inventor: Shyam Ramakrishnan, Brighton, MA (US)

(73) Assignee: Bayer Healthcare AG, Leverkusen (DE)

( * ) Notice: Subject to any disclaimer, the term of this patent is extended or adjusted under 35 U.S.C. 154(b) by 0 days.

(21) Appl. No.: 11/357,125

(22) Filed: Feb. 21, 2006

(65) Prior Publication Data

US 2006/0141552 A1 Jun. 29, 2006

Related U.S. Application Data

(63) Continuation of application No. 10/311,954, filed as application No. PCT/EP01/07287 on Jun. 26, 2001, now abandoned.

(60) Provisional application No. 60/214,009, filed on Jun. 26, 2000.

(51) Int. Cl.
*C12Q 1/37* (2006.01)
*C12Q 1/68* (2006.01)
*C07H 21/04* (2006.01)
*C12N 9/64* (2006.01)

(52) U.S. Cl. ..................... 435/23; 435/219; 435/69.1; 435/320.1; 435/226; 536/23.1

(58) Field of Classification Search .................. 435/15, 435/193
See application file for complete search history.

(56) References Cited

U.S. PATENT DOCUMENTS 5,654,146 A * 8/1997 Braxton et al. ................. 435/6
5,858,778 A 1/1999 Alnemri et al.
5,869,315 A * 2/1999 Talanian et al. ............. 435/226

OTHER PUBLICATIONS

Alnemri et al., "Cloning and expression of four novel isoforms of human interleukin-1 beta converting enzyme with different apoptotic activities", *J. Biol Chem* Mar. 3, 1995; 270(9):4312-4317.

Stosic-Grujicic et al., "Modulatory in vitro effects of interleukin-1 receptor antagonist (IL-1Ra) or antisense oligonucleotide to interleukin-1 beta converting enzyme (ICE) on acute myeloid leukaemia (AML) cell growth", *Clin Lab Haematol.* Jun. 1999;21 (3):173-85.

Estrov et al., "Role of interleukin-1 beta converting enzyme (ICE) in leukemia", *Cytokines Mol Ther.* Mar. 1996; 2(1):1-11.

Zhu et al., "Increased interleukin-1beta converting enzyme expression and activity in Alzheimer disease", *J Neuropathol Exp Neurol.* Jun. 1999; 58(6):582-7.

Masliah et al., "Caspase dependent DNA fragmentation might be associated with excitotoxicity in Alzheimer diease", *J Neuropathol Exp Neurol.* Nov. 1998; 57(11):1041-52.

Suzuki, "Amyloid beta-protein induces necrotic cell death mediated by ICE cascade in PC12 cells", *Exp Cell Res.* Aug. 1, 1997; 234(2):507-11.

Garcia-Calvo et al., "Purification and catalytic properties of human caspase family members", Cell Death and Differnti, 1999, 6, pp. 362-369.

Wilson et al., "Structure and mechanism of interleukin-1β converting enzyme", Nature, 370, 1999, pp. 270-275.

Romanowski et al., "Crystal structures of a ligand-free and malonate-bound human caspase-1: Implications for the mechanism of substrate binding", Structure, vol. 12, 2004, pp. 1361-1371.

Concha et al., "Controlling apoptosis by inhibition of caspase", Current Medicinal Chemistry, 2002, 9, pp. 713-726.

Database Swall [Online] Apr. 1, 1993 Thornberry, N.A.., et al.: "Interleukin-1 Beta Convertase (IL-1BC) (EC 3.4.22.36)" retrieved from EBI Database accession No. P29466 (XP002192392.

Database EMBL [Online] Oct. 10, 1998 Robert Strausberg: "similar to gb:M87507 Interleukin-1 Beta Convertase Precursor (Human)" retrieved from EBI Database accession No. A1189378 (XP002192390.

Database EMBL [Online] Oct. 28, 1998 Robert Strausberg: "similar to gb:M87507 Interleukin-1 Beta Convertase" retrieved from RBI Database accession No. AI220630 (XP002192391.

Cohen et al., J. Biochem, 1997, 326, pp. 1-16.

* cited by examiner

*Primary Examiner*—Rebecca E. Prouty
*Assistant Examiner*—Md. Meah
(74) *Attorney, Agent, or Firm*—Banner & Witcoff, Ltd.

(57) ABSTRACT

Screening methods to identify candidate therapeutic agents using a newly identified human caspases-1-like protease.

3 Claims, 9 Drawing Sheets

Fig. 1

| | | | |
|---|---|---|---|
| ttttttttt | tttgaaagga | aactgggtag | ttctttattg |
| taaagggcag | aaacgtgcaa | ttacagattg | tgaaactgct |
| gcttagaatt | ccaggctcat | tgtaaggaag | tgccttgtcg |
| tcagcaagtt | gacatccaag | tactggaact | tagtttcttc |
| cggccctcag | acattcatac | agcttcctta | ttttaatgta |
| ctgggaagag | atagaaacgt | cttgtcgaag | taactctttc |
| agtgctggc | atctgtgctt | tatcatctgg | ctgctcaaat |
| gaaagttgaa | cctaatgtgg | aagagcagaa | agcaataaaa |
| tccttctcta | tgtgtacttg | attaatagca | tcatcctcaa |
| aatctcccgg | agttggtaaa | gatatatttt | cagaggccgg |
| tactgaatct | tttaccaaca | ccacaccatg | g |

Fig. 2

HGVVLVKDSVPASENISLPTPGDFEDDAINQVHIEKDFIAFCSSTL
G//VQLSFEQPDDKAQMPSTERVTSTRRFYLFPVH

Fig. 3 ttttttttttt	tgaaaggaaa	ctgtgtattt	ctttattgta
aagggcagaa	acgtgcaattacagattgtg	aaactgctgc
ttagaattcc	aggctcattg	taaggaagtg	ccttgtcgtc
agcaagttga	catccaagta	ctggaactta	gtttcttccg
gccctcagac	attcatacag	cttccttatt	ttaatgtact
gggaagagat	agaaacgtct	tgtcgaagta	actctttcag
tgctgggcat	ctgtgcttta	tcatctggct	gctcaaatga
aagttgaacc	taatgtggaa	gagcagaaag	caataaaatc
cttctctatg	tgtacttgat	taatagcatc	atcctcaaaatct

Fig. 4

MADKVLKEKR KLFIRSMGEG TINGLLDELL QTRVLNKEEM
EKVKRENATV MDKTRALIDS VIPKGAQACQ ICITYICEED
SYLAGTLGLS ADQTSGNYLN MQDSQGVLSS FPAPQAVQDN
PAMPTSSGSE GNVKLCSLEE AQRIWKQKSA EIYPIMDKSS
RTRLALIICN EEFDSIPRRT GAEVDITGMT MLLQNLGYSV
DVKKNLTASD MTTELEAFAH RPEHKTSDST FLVFMSHGIR
EGICGKKHSE QVPDILQLNA IFNMLNTKNC PSLKDKPKVI
IIQACRGDSP GVVWFKDSVG VSGNLSLPTT EEFEDDAIKK
AHIEKDFIAF CSSTPDNVSW RHPTMGSVFI GRLIEHMQEY
ACSCDVEEIF RKVRFSFEQP DGRAQMPTTE RVTLTRCFYL
FPGH

Fig. 5

```
BLASTP - Query = AI189378_TR; Hit = swissnew|P29466|I1BC_HUMAN

This hit is scoring at : 6e-20 (expectation value)

Alignment length (overlap) : 114

Identities : 50 %

Scoring matrix : BLOSUM62 (used to infer consensus pattern)

Database searched : nrdb

Q:   2 GVVLVKDSVPASENISLPTPGDFEDDAINQVHIEKDFIAFCSST------LG----   79
         GVV .KDSV .S N:SLPT. :FEDDAI.:.HIEKDFIAFCSST           :G
H: 291 GVVWFKDSVGVSGNLSLPTTEEFEDDAIKKAHIEKDFIAFCSSTPDNVSWRHPTMGSVFI  404

VQLSFEQPDDKAQMPSTERVTSTRRFYLFPVH
                       V..SFEQPD.:AQMP:TERVT TR FYLFP H
                       GRLIEHMQEYACSCDVEEIFRKVRFSFEQPDGRAQMPTTERVLTRCFYLFPGH

HMMPFAM ICE-like protease (caspase) p10 domain
```

Fig. 6

HMMPFAM - alignment of 116_TR against pfam|hmm|ICE_p10

ICE-like protease (caspase) p10 domain

This hit is scoring at : 17.7; Expect = 0.0032

Scoring matrix : BLOSUM62 (used to infer consensus pattern)

Q: 28 AINQVHIEKDFIAFCSST 45

A: :: :E.DF:AF S:T

H: 1 avyKiPveaDflafyStt 18

Fig. 7

HMMPFAM - alignment of 116_TR against pfam|hmm|ICE_p10

ICE-like protease (caspase) p10 domain

This hit is scoring at : 28.4; Expect = 4.7e-06

Scoring matrix : BLOSUM62 (used to infer consensus pattern)

```
Q:  48 VQLSFE-------QPDDKAQMPSTERVTSTRRFYLFP      77

V  .       QP  :: :.  ..ER T T::.YLFP

H:  57 VnkkvareregfckdqpfnrkKqipcerstLtkklYlFP    95
```

Fig. 8

Expression of IL-1-beta converting enzyme and human Caspase-1-like protease in the immune and airway system

= A: IL-1βC
= B: LBRI 116

| | IL-1βC | Caspase-1-like protease | | | IL-1βC | Caspase-1-like protease |
|---|---|---|---|---|---|---|
| 1. PBMN | - | - | 13 Neutrophil | | ++ | + |
| 2. PBMN activated | - | - | 14 Eosinophil | | - | - |
| 3. CD8+ | - | - | 15 BL2 B cell/α-CD40+IL-4 0h | | - | - |
| 4. CD8+ activated | - | - | 16 BL2 B cell/α-CD40+IL-4 4h | | - | - |
| 5. CD4+ | - | - | 17 BL2 B cell/α-CD40+IL-4 24h | | - | - |
| 6. CD4+ activated | - | - | 18 Jurkat/PMA+IOM 0h | | - | - |
| 7. CD19 | - | - | 19 Jurkat/PMA+IOM 0h | | - | - |
| 8. CD19+ activated | - | - | 20 Jurkat/PMA+IOM 0h | | - | - |
| 9. Monocyte | + | - | 21 PBMC | | + | ± |
| 10. Th1 clone | - | - | 22 Lung epithelial | | - | - |
| 11. Th2 clone | - | + | 23 BSMC | | - | - |
| 12. - | | | 24 NHLF | | - | - |

REGULATION OF HUMAN CASPASE-1-LIKE PROTEASE

This application is a continuation of Ser. No. 10/311,954 filed Dec. 20, 2002, now abandoned which is a National Stage application of co-pending PCT application PCT/EP01/07287 filed Jun. 26, 2001, which was published in English under PCT Article 21(2) on Jan. 3, 2002, and which claims the benefit of U.S. provisional application Ser. No. 60/214,009 filed Jun. 26, 2000. Each of these applications is incorporated herein by reference in its entirety.

TECHNICAL FIELD OF THE INVENTION

The invention relates to the area of regulation human caspase-1-like protease activity to provide therapeutic effects.

BACKGROUND OF THE INVENTION

Interleukin-1 beta-converting enzyme (ICE, caspase-1) activates the proinflammatory cytokines interleukin (IL)-1beta and IL-18, or by mediating apoptotic processes and therefore is involved in regulation of important steps in inflammation and immunity (Young et al., *J. Exp. Med.* 191, 1535–44, 2000). Because of the importance of these processes in a variety of disease processes, there is a need in the art to identify additional caspase-1-like enzymes whose activity can be regulated to provide therapeutic effects.

SUMMARY OF THE INVENTION

It is an object of the invention to provide reagents and methods of regulating human caspase-1-like protease. These and other objects of the invention are provided by one or more of the embodiments described below.

One embodiment of the invention is a caspase-1-like protease polypeptide comprising an amino acid sequence selected from the group consisting of: amino acid sequences which are at least about 60% identical to the amino acid sequence shown in SEQ ID NO: 2; the amino acid sequence shown in SEQ ID NO: 2;

amino acid sequences which are at least about 60% identical to the amino acid sequence shown in SEQ ID NO: 6; and the amino acid sequence shown in SEQ ID NO: 6.

Yet another embodiment of the invention is a method of screening for agents which decrease extracellular matrix degradation. A test compound is contacted with a caspase-1-like protease polypeptide comprising an amino acid sequence selected from the group consisting of:

amino acid sequences which are at least about 60% identical to the amino acid sequence shown in SEQ ID NO: 2;

the amino acid sequence shown in SEQ ID NO: 2;

amino acid sequences which are at least about 60% identical to the amino acid sequence shown in SEQ ID NO: 6; and the amino acid sequence shown in SEQ ID NO: 6.

Binding between the test compound and the caspase-1-like protease is polypeptide detected. A test compound which binds to the caspase-1-like protease polypeptide is thereby identified as a potential agent for decreasing extracellular matrix degradation. The agent can work by decreasing the activity of the caspase-1-like protease.

Another embodiment of the invention is a method of screening for agents which decrease extracellular matrix degradation. A test compound is contacted with a polynucleotide encoding a caspase-1-like protease polypeptide, wherein the polynucleotide comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 3;

the nucleotide sequence shown in SEQ ID NO: 3;

nucleotide sequences which are at least about 50% identical to the nucleotide sequence shown in SEQ ID NO: 5; and the nucleotide sequence shown in SEQ ID NO: 5.

Binding of the test compound to the polynucleotide is detected. A test compound which binds to the polynucleotide is identified as a potential agent for decreasing extracellular matrix degradation. The agent can work by decreasing the amount of the caspase-1-like protease through interacting with the caspase-1-like protease mRNA.

Another embodiment of the invention is a method of screening for agents which regulate extracellular matrix degradation. A test compound is contacted with a caspase-1-like protease polypeptide comprising an amino acid sequence selected from the group consisting of:

amino acid sequences which are at least about 60% identical to the amino acid sequence shown in SEQ ID NO: 2;

the amino acid sequence shown in SEQ ID NO: 2;

amino acid sequences which are at least about 60% identical to the amino acid sequence shown in SEQ ID NO: 6; and the amino acid sequence shown in SEQ ID NO: 6.

A caspase-1-like protease activity of the polypeptide is detected. A test compound which increases caspase-1-like protease activity of the polypeptide relative to caspase-1-like protease activity in the absence of the test compound is thereby identified as a potential agent for increasing extracellular matrix degradation. A test compound which decreases caspase-1-like protease activity of the polypeptide relative to caspase-1-like protease activity in the absence of the test compound is thereby identified as a potential agent for decreasing extracellular matrix degradation.

Even another embodiment of the invention is a method of screening for agents which decrease extracellular matrix degradation. A test compound is contacted with a caspase-1-like protease product of a polynucleotide which comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 3;

the nucleotide sequence shown in SEQ ID NO: 3;

nucleotide sequences which are at least about 50% identical to the nucleotide sequence shown in SEQ ID NO: 5; and the nucleotide sequence shown in SEQ ID NO: 5.

Binding of the test compound to the caspase-1-like protease product is detected. A test compound which binds to the caspase-1-like protease product is thereby identified as a potential agent for decreasing extracellular matrix degradation.

Still another embodiment of the invention is a method of reducing extracellular matrix degradation. A cell is contacted with a reagent which specifically binds to a polynucleotide encoding a caspase-1-like protease polypeptide or the product encoded by the polynucleotide, wherein the polynucleotide comprises a nucleotide sequence selected from the group consisting of:

nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 3;
the nucleotide sequence shown in SEQ ID NO: 3;
nucleotide sequences which are at least about 50% identical to the nucleotide sequence shown in SEQ ID NO: 5; and
the nucleotide sequence shown in SEQ ID NO: 5.

Caspase-1-like protease activity in the cell is thereby decreased.

The invention thus provides reagents and methods for regulating human caspase-1-like protease activity which can be used inter alia, to treat an allergic disease, asthma, cancer and neurodegenerative diseases.

BRIEF DESCRIPTION OF THE DRAWINGS

FIG. 1 shows the DNA-sequence encoding a caspase-1-like protease polypeptide (SEQ ID NO: 1).

FIG. 2 shows the amino acid sequence deduced from the DNA-sequence of FIG. 1 (SEQ ID NO: 2).

FIG. 3 shows the DNA-sequence encoding a caspase-1-like protease polypeptide (SEQ ID NO: 3).

FIG. 4 shows the amino acid sequence of the protein identified by SwissProt Accession No. P29466 (SEQ ID NO:4).

FIG. 5 shows the BLASTX alignment of caspase-1-like protease as shown in SEQ ID NO: 2 with the human protein identified by SwissProt Accession No. P29466 (SEQ ID NO:4).

FIG. 6 shows the HMMPFAM—alignment of caspase-1 (SEQ ID NO:2) against pfam|hmm|ICE_p10.

FIG. 7 shows the HMMPFAM—alignment of caspase-1 (SEQ ID NO:2) against pfam|hmm|ICE_p10.

FIG. 8 shows the results of gene expression profiling of human caspase-1 like protease in various tissues.

DETAILED DESCRIPTION OF THE INVENTION

Figure 9:
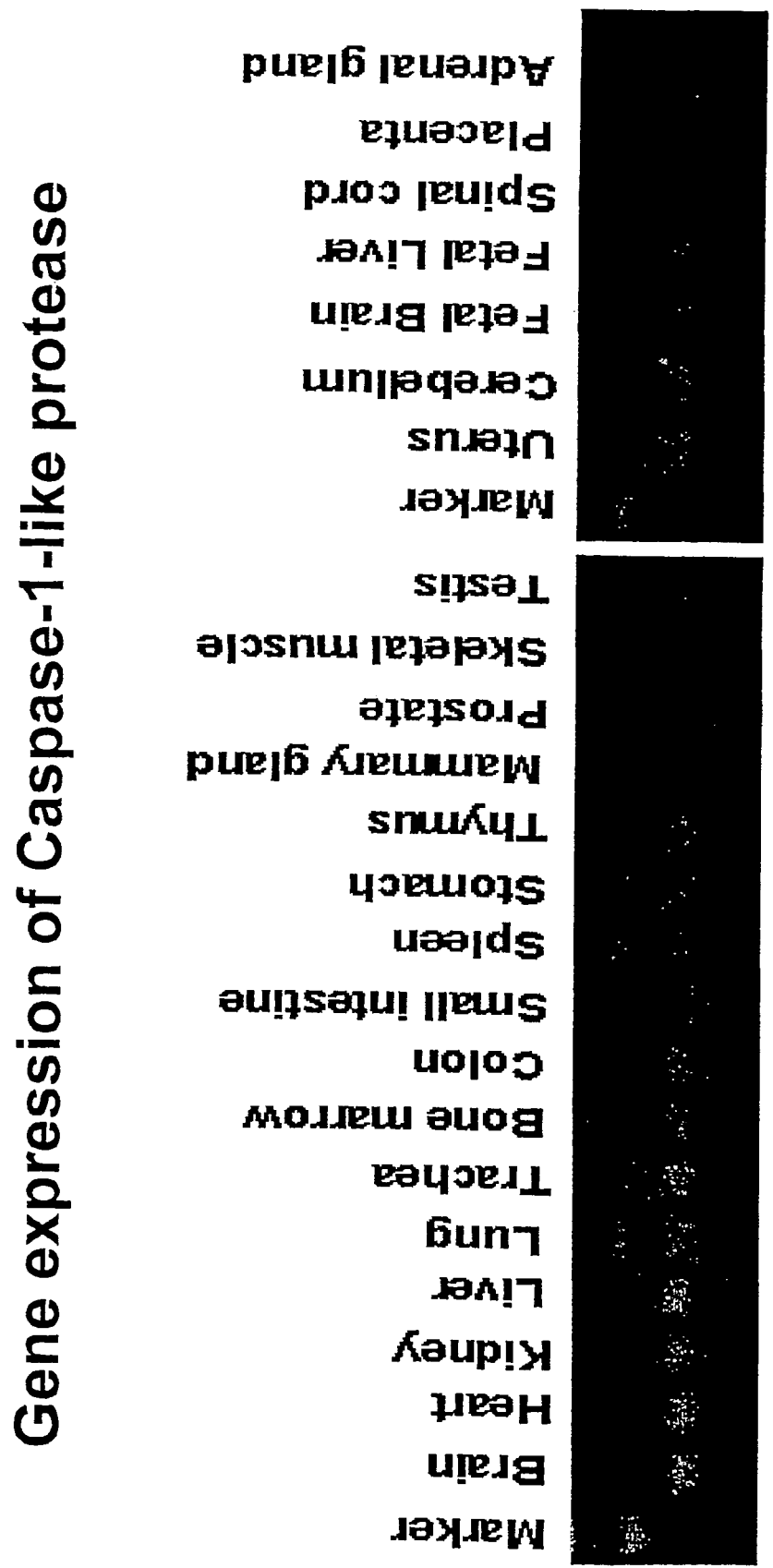
FIG. 9 shows the results of gene expression profiling of human caspase-1 like protease in immune-related and airway system cells.

The invention relates to an isolated polynucleotide encoding a caspase-1-like protease polypeptide and being selected from the group consisting of:
a) a polynucleotide encoding a caspase-1-like protease polypeptide comprising an amino acid sequence selected from the group consisting of:
amino acid sequences which are at least about 60% identical to
the amino acid sequence shown in SEQ ID NO: 2;
the amino acid sequence shown in SEQ ID NO: 2;
amino acid sequences which are at least about 60% identical to
the amino acid sequence shown in SEQ ID NO: 6; and
the amino acid sequence shown in SEQ ID NO: 6.
b) a polynucleotide comprising the sequence of SEQ ID NOS: 1, 3 or 5;
c) a polynucleotide which hybridizes under stringent conditions to a polynucleotide specified in (a) and (b);
d) a polynucleotide the sequence of which deviates from the polynucleotide sequences specified in (a) to (c) due to the degeneration of the genetic code; and
e) a polynucleotide which represents a fragment, derivative or allelic variation of a polynucleotide sequence specified in (a) to (d).

Furthermore, it has been discovered by the present applicant that activity of a caspase-1-like protease, particularly a human caspase-1-like protease, can be used to treat an allergic disease, asthma, cancer and neurodegenerative diseases such as Alzheimer's disease. Human caspase-1-like protease can also be used to treat immune-related diseases, such as inflammatory diseases and allergic diseases including asthma, allergic rhinitis; atopic dermatitis; hives; conjunctivitis; vernal catarrh; chronic arthrorheumatism; systemic lupus erythematosus; psoriasis; diabrotic colitis; systemic inflammatory response syndrome (SIRS); sepsis; polymyositis; dermatomyositis (DM); Polyaritis nodoa (PN); mixed connective tissue disease (MCTD); Sjoegren's syndrome; and gout. Human caspase-1-like protease as shown in SEQ ID NO:2 or 6 contains an ICE-like protease p10 domain and is 50% identical to the human protein identified by SwissProt Accession No. O96009 (SEQ ID NO:4) and annotated as capsase-1 (FIG. 1). Human caspase-1-like protease is therefore expected to be useful for the same purposes as previously identified caspases.

Polypeptides

Caspase-1-like protease polypeptides according to the invention comprise at least 10, 15, 25, 50, or 75 contiguous amino acids selected from SEQ ID NO:2 or 6 or from a biologically active variant thereof, as defined below. An caspase-1-like protease polypeptide of the invention therefore can be a portion of an caspase-1-like protease molecule, a full-length caspase-1-like protease molecule, or a fusion protein comprising all or a portion of an caspase-1-like protease molecule.

Biologically Active Variants

Caspase-1-like protease variants which are biologically active, i.e., retain an caspase-1-like protease activity, also are caspase-1-like protease polypeptides. Preferably, naturally or non-naturally occurring caspase-1-like protease variants have amino acid sequences which are at least about 50, 55, 60, 65, 70, more preferably about 75, 80, 85, 90, 96, or 98% identical to the amino acid sequence shown in SEQ ID NO:2 or 6. Percent identity between a putative caspase-1-like protease variant and an amino acid sequence of SEQ ID NO:2 or 6 is determined with the Needleman/Wunsch algorithm (Needleman and Wunsch, J. Mol. Biol. 48; 443–453, 1970) using a Blosum62 matrix with a gap creation penalty of 8 and a gap extension penalty of 2 (S. Henikoff and J. G. Henikoff, Proc. Natl. Acad. Sci. USA 89:10915–10919, 1992).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity can be found using computer programs well known in the art, such as DNASTAR software. Whether an amino acid change results in a biologically active caspase-1-like protease polypeptide can readily be determined by assaying for fibronectin binding or for caspase-1-like protease activity, as is known in the art and described, for example, in Example 2.

Fusion Proteins

Fusion proteins are useful for generating antibodies against caspase-1-like protease amino acid sequences and for use in various assay systems. For example, fusion proteins can be used to identify proteins which interact with portions of an caspase-1-like protease polypeptide, including its active site and fibronectin domains. Methods such as protein affinity chromatography or library-based assays for protein-protein interactions, such as the yeast two-hybrid or phage display systems, can be used for this purpose. Such methods are well known in the art and also can be used as drug screens.

An caspase-1-like protease fusion protein comprises two protein segments fused together by means of a peptide bond. For example, the first protein segment can comprise at least 10, 15, 25, 50, or 75 contiguous amino acids selected from SEQ ID NO:2 or 6 or a biologically active variant thereof.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (A) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the caspase-1-like protease polypeptide-encoding sequence and the heterologous protein sequence, so that the caspase-1-like protease polypeptide can be cleaved and purified away from the heterologous moiety.

A fusion protein can be synthesized chemically, as is known in the art. Preferably, a fusion protein is produced by covalently linking two protein segments or by standard procedures in the art of molecular biology. Recombinant DNA methods can be used to prepare fusion proteins, for example, by making a DNA construct which comprises caspase-1-like protease coding sequences disclosed herein in proper reading frame with nucleotides encoding the second protein segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human caspase-1-like protease can be obtained using caspase-1-like protease polynucleotides (described below) to make suitable probes or primers to screening cDNA expression libraries from other species, such as mice, monkeys, or yeast, identifying cDNAs which encode homologs of caspase-1-like protease, and expressing the cDNAs as is known in the art.

Polynucleotides

An caspase-1-like protease polynucleotide can be single- or double-stranded and comprises a coding sequence or the complement of a coding sequence for an caspase-1-like protease polypeptide. The coding sequence for a caspase-1-like protease is shown in SEQ ID NO:5. The complement of a coding sequence for the caspase-1-like protease of SEQ ID NO:2 is shown in SEQ ID NO:1. The EST shown in SEQ ID NO:1 encompasses the EST shown in SEQ ID NO:3. There are three genomic clones which comprise SEQ ID NO:1: emnew AC027011, embl AP001153, and embl AP000799.

Degenerate nucleotide sequences encoding human caspase-1-like protease polypeptides, as well as homologous nucleotide sequences which are at least about 50, 55, 60, 65, or 70, more preferably about 75, 90, 96, or 98% identical to the complement of the caspase-1-like protease sequences shown in SEQ ID NOS:1, 3 and 5 also are caspase-1-like protease polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of caspase-1-like protease polynucleotides which encode biologically active caspase-1-like protease polypeptides also are caspase-1-like protease polynucleotides.

Identification of Variants and Homologs

Variants and homologs of the caspase-1-like protease polynucleotides disclosed above also are caspase-1-like protease polynucleotides. Typically, homologous caspase-1-like protease polynucleotide sequences can be identified by hybridization of candidate polynucleotides to known caspase-1-like protease polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the caspase-1-like protease polynucleotides disclosed herein can be identified by making suitable probes or primers and screening cDNA expression libraries from other species, such as mice, monkeys, or yeast. Human variants of caspase-1-like protease polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human caspase-1-like protease polynucleotides or caspase-1-like protease polynucleotides of other species can therefore be identified, for example, by hybridizing a putative homologous caspase-1-like protease polynucleotide with a polynucleotide having a nucleotide sequence of SEQ ID NO:1 or 5 or its complement to form a test hybrid. The melting temperature of the test hybrid is compared with the melting temperature of a hybrid comprising caspase-1-like protease polynucleotides having perfectly complementary nucleotide sequences, and the number or percent of basepair mismatches within the test hybrid is calculated.

Nucleotide sequences which hybridize to caspase-1-like protease polynucleotides or their complements following stringent hybridization and/or wash conditions are also caspase-1-like protease polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between an caspase-1-like protease polynucleotide having a coding sequence disclosed herein and a polynucleotide sequence which is at least about 50, 55, 60, 65, 70, more preferably about 75, 90, 96, or 98% identical to that nucleotide sequence can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% G+C) - 0.63(\% \text{ formamide}) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring caspase-1-like protease polynucleotide can be isolated free of other cellular components such as membrane components, proteins, and lipids. Polynucleotides can be made by a cell and isolated using standard nucleic acid purification techniques, synthesized using an amplification technique, such as the polymerase chain reaction PCR), or synthesized using an automatic synthesizer. Methods for isolating polynucleotides are routine and are known in the art. Any such technique for obtaining a polynucleotide can be used to obtain isolated caspase-1-like protease polynucleotides. For example, restriction enzymes and probes can be used to isolate polynucleotide fragments which comprise caspase-1-like protease nucleotide sequences. Isolated polynucleotides are in preparations which are free or at least 70, 80, or 90% free of other molecules.

Caspase-1-like protease cDNA molecules can be made with standard molecular biology techniques, using caspase-1-like protease mRNA as a template. Caspase-1-like protease cDNA molecules can thereafter be replicated using molecular biology techniques known in the art and disclosed in manuals such as Sambrook et al. (1989). An amplification technique, such as PCR, can be used to obtain additional copies of caspase-1-like protease polynucleotides, using either human genomic DNA or cDNA as a template.

Alternatively, synthetic chemistry techniques can be used to synthesize caspase-1-like protease polynucleotides. The degeneracy of the genetic code allows alternate nucleotide sequences to be synthesized which will encode an caspase-1-like protease polypeptide having, for example, the amino acid sequence shown in SEQ ID NO:2 or 6 or a biologically active variant of that sequence.

Extending Polynucleotides

Various PCR-based methods can be used to extend the nucleic acid sequences encoding the disclosed portions of human caspase-1-like protease to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations are used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991. Additionally, PCR, nested primers, and PROMOTERFINDER libraries (CLONTECH, Palo Alto, Calif.) can be used to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Expression Profiling

Expression profiling is based on a quantitative polymerase chain reaction (PCR) analysis, also called kinetic analysis, first described in Higuchi et al., 1992 and Higuchi et al., 1993. The principle is that at any given cycle within the exponential phase of PCR, the amount of product is proportional to the initial number of template copies. Using this technique, the expression levels of particular genes, which are transcribed from the chromosomes as messenger RNA (mRNA), are measured by first making a DNA copy (cDNA) of the mRNA, and then performing quantitative PCR on the cDNA, a method called quantitative reverse transcription-polymerase chain reaction (quantitative RT-PCR).

Obtaining Polypeptides

Caspase-1-like protease polypeptides can be obtained, for example, by purification from cells, by expression of caspase-1-like protease polynucleotides, or by direct chemical synthesis.

Protein Purification

Caspase-1-like protease polypeptides can be purified from cells, such as 8–9 week placental cells, primary tumor cells, metastatic cells, or cancer cell lines (e.g., colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, or the H392 glioblastoma cell line), as well as cells transfected with an caspase-1-like protease expression construct. Squamous cell carcinomas are especially useful sources of caspase-1-like protease polypeptides. A purified caspase-1-like protease polypeptide is separated from other compounds which normally associate with the caspase-1-like protease polypeptide in the cell, such as certain proteins, carbohydrates or lipids, using methods well-known in the art. Such methods include, but are not limited to, size exclusion chromatography, ammonium sulfate fractionation, ion exchange chromatography, affinity chromatography, and preparative gel electrophoresis. A preparation of purified caspase-1-like protease polypeptides is at least 80% pure; preferably, the preparations are 90%, 95%, or 99% pure. Purity of the preparations can be assessed by any means known in the art, such as SDS-polyacrylamide gel electrophoresis. Enzymatic activity of the purified preparations can be assayed, for example, as described in Young et al., *J. Exp. Med.* 191, 1535–44 (2000).

Expression of Polynucleotides

To express an caspase-1-like protease polypeptide, an caspase-1-like protease polynucleotide can be inserted into an expression vector which contains the necessary elements for the transcription and translation of the inserted coding sequence. Methods which are well known to those skilled in the art can be used to construct expression vectors containing sequences encoding caspase-1-like protease polypeptides and appropriate transcriptional and translational control elements. These methods include in vitro recombinant DNA techniques, synthetic techniques, and in vivo genetic recombination. Such techniques are described, for example, in Sambrook et al. (1989) and Ausubel et al., CURRENT PROTOCOLS IN MOLECULAR BIOLOGY, John Wiley & Sons, New York, N.Y., 1989.

A variety of expression vector/host systems can be utilized to contain and express sequences encoding an caspase-1-like protease polypeptide. These include, but are not limited to, microorganisms, such as bacteria transformed with recombinant bacteriophage, plasmid, or cosmid DNA expression vectors; yeast transformed with yeast expression vectors; insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, La Jolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an caspase-1-like protease polypeptide, vectors based on SV40 or EBV can be used with an appropriate selectable marker.

Bacterial and Yeast Expression Systems

In bacterial systems, a number of expression vectors can be selected depending upon the use intended for the caspase-1-like protease polypeptide. For example, when a large quantity of an caspase-1-like protease polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene), in which the sequence encoding the caspase-1-like protease polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989 or pGEX vectors (Promega, Madison, Wis.) can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or Factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding caspase-1-like protease polypeptides can be driven by any of a number of promoters. For example, viral promoters such as the 35S and 19S promoters of CaMV can be used alone or in combination with the omega leader sequence from TMV (Takamatsu *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (see, for example, Hobbs or Murray, in McGraw Hill Yearbook of Science and Technology, McGraw Hill, New York, N.Y., pp. 191–196, 1992).

An insect system also can be used to express an caspase-1-like protease polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding caspase-1-like protease polypeptides can be cloned into a non-essential region of the virus, such as the polyhedrin gene, and placed under control of the polyhedrin promoter. Successful insertion of caspase-1-like protease polypeptides will render the polyhedrin gene inactive and produce recombinant virus lacking coat protein The recombinant viruses can then be used to infect, for example, *S. frugiperda* cells or *Trichoplusia* larvae in which caspase-1-like protease polypeptides can be expressed (Engelhard et al., *Proc. Nat. Acad. Sci.* 91, 3224–3227, 1994).

Mammalian Expression Systems

A number of viral-based expression systems can be utilized in mammalian host cells. For example, if an adenovirus is used as an expression vector, sequences encoding caspase-1-like protease polypeptides can be ligated into an adenovirus transcription/translation complex consisting of the late promoter and tripartite leader sequence. Insertion in a non-essential E1 or E3 region of the viral genome can be used to obtain a viable virus which is capable of expressing an caspase-1-like protease polypeptide in infected host cells (Logan & Shenk, *Proc. Natl. Acad. Sci.* 81, 3655–3659, 1984). In addition, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding caspase-1-like protease polypeptides. Such signals include the ATG initiation codon and adjacent sequences. In cases where sequences encoding an caspase-1-like protease polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process an expressed caspase-1-like protease polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express caspase-1-like protease polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced caspase-1-like protease sequences. Resistant clones of stably transformed cells can be proliferated using tissue culture techniques appropriate to the cell type.

Any number of selection systems can be used to recover transformed cell lines. These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980). Genes which can be employed in $tk^-$ or $aprt^-$ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980); npt confers resistance to the aminoglycosides, neomycin and G-418 (Colbere-Garapin et al., *J. Mol. Biol.* 150, 1–14, 1981); and als and pat confer resistance to chlorsulfuron and phosphinotricin acetyltransferase, respectively (Murray, 1992 supra). Additional selectable genes have been described, for example trpB, which allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression of Polypeptides

Although the presence of marker gene expression suggests that the caspase-1-like protease polynucleotide is also present, its presence and expression may need to be confirmed. For example, if a sequence encoding an caspase-1-like protease polypeptide is inserted within a marker gene sequence, transformed cells containing sequences which encode an caspase-1-like protease polypeptide can be identified by the absence of marker gene function. Alternatively, a marker gene can be placed in tandem with a sequence encoding an caspase-1-like protease polypeptide under the control of a single promoter. Expression of the marker gene in response to induction or selection usually indicates expression of the caspase-1-like protease polynucleotide.

Alternatively, host cells which contain an caspase-1-like protease polynucleotide and which express an caspase-1-like protease polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein.

The presence of a polynucleotide sequence encoding an caspase-1-like protease polypeptide can be detected by DNA-DNA or DNA-RNA hybridization or amplification using probes or fragments or fragments of polynucleotides encoding an caspase-1-like protease polypeptide. Nucleic acid amplification-based assays involve the use of oligonucleotides selected from sequences encoding an caspase-1-like protease polypeptide to detect transformants which contain an caspase-1-like protease polynucleotide.

A variety of protocols for detecting and measuring the expression of an caspase-1-like protease polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on an caspase-1-like protease polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding caspase-1-like protease polypeptides include oligolabeling, nick translation, end-labeling, or PCR amplification using a labeled nucleotide. Alternatively, sequences encoding an caspase-1-like protease polypeptide can be cloned into a vector for the production of an mRNA probe. Such vectors are known in the art, are commercially available, and can be used to synthesize RNA probes in vitro by addition of labeled nucleotides and an appropriate RNA polymerase, such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, fluorescent, chemiluminescent, or chromogenic agents, as well as substrates, cofactors, inhibitors, magnetic particles, and the like.

Expression and Purification of Polypeptides

Host cells transformed with nucleotide sequences encoding an caspase-1-like protease polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode caspase-1-like protease polypeptides can be designed to contain signal sequences which direct secretion of caspase-1-like protease polypeptides through a prokaryotic or eukaryotic cell membrane.

Other constructions can be used to join a sequence encoding an caspase-1-like protease polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen, San Diego, Calif.) between the purification domain and the caspase-1-like protease polypeptide can be used to facilitate purification. One such expression vector provides for expression of a fusion protein containing an caspase-1-like protease polypeptide and 6 histidine residues preceding a thioredoxin or an enterokinase cleavage site. The histidine residues facilitate purification on IMAC (immobilized metal ion affinity chromatography as described in Porath et al., *Prot. Exp. Purif.* 3, 263–281, 1992), while the enterokinase cleavage site provides a means for purifying the caspase-1-like protease polypeptide from the fusion protein. Vectors which contain fusion proteins are disclosed in Kroll et al., *DNA Cell Biol.* 12, 441–453, 1993).

Chemical Synthesis

Sequences encoding an caspase-1-like protease polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, an caspase-1-like protease polypeptide itself can be produced using chemical methods to synthesize its amino acid sequence. For example, caspase-1-like protease polypeptides can be produced by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Various fragments of caspase-1-like protease polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic caspase-1-like protease polypeptide can be confirmed by amino acid analysis or sequencing (e.g., the Edman degradation procedure; see Creighton, supra). Additionally, any portion of the amino acid sequence of the caspase-1-like protease polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce caspase-1-like protease polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter caspase-1-like protease polypeptide-encoding sequences for a variety of reasons, including modification of the cloning, processing, and/or expression of the gene product. DNA shuffling by random fragmentation and, PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of an caspase-1-like protease polypeptide. "Antibody" as used herein includes intact immunoglobulin molecules, as well as fragments thereof, such as Fab, F(ab')$_2$, and Fv, which are capable of binding an epitope of an caspase-1-like protease polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an caspase-1-like protease polypeptide can be used therapeutically, as well as in immunochemical assays, including but not limited to Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art Such immunoassays typically involve the measurement of complex formation between an immunogen and an antibody which specifically binds to the immunogen.

Typically, an antibody which specifically binds to an caspase-1-like protease polypeptide provides a detection signal at least 5-, 10-, or 20-fold higher than a detection signal provided with other proteins when used in an immunochemical assay. Preferably, antibodies which specifically bind to caspase-1-like protease polypeptides do not detect other proteins in immunochemical assays and can immunoprecipitate an caspase-1-like protease polypeptide from solution.

Caspase-1-like protease polypeptides can be used to immunize a mammal, such as a mouse, rat, rabbit, guinea pig, monkey, or human, to produce polyclonal antibodies. If desired, an caspase-1-like protease polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies which specifically bind to an caspase-1-like protease polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, one can produce humanized antibodies using recombinant methods, as described in GB2188638B. Antibodies which specifically bind to an caspase-1-like protease polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to caspase-1-like protease polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61, 497–501; Nicholls et al., 1993, *J. Immunol. Meth.* 165, 81–91.

Antibodies which specifically bind to caspase-1-like protease polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies of the invention can be purified by methods well known in the art. For example, antibodies can be affinity purified by passage over a column to which an caspase-1-like protease polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of caspase-1-like protease gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, Meth. Mol. Biol. 20, 1–8, 1994; Sonveaux, Meth. Mol. Biol. 26, 1–72, 1994; Uhlmann et al., Chem. Rev. 90, 543–583, 1990.

Modifications of caspase-1-like protease gene expression can be obtained by designing antisense oligonucleotides which will form duplexes to the control, 5', or regulatory regions of the caspase-1-like protease gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLCULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful duplex formation between an antisense oligonucleotide and the complementary sequence of an caspase-1-like protease polynucleotide. Antisense oligonucleotides which comprise, for example, 2, 3, 4, or 5 or more stretches of contiguous nucleotides which are precisely complementary to an caspase-1-like protease polynucleotide, each separated by a stretch of contiguous nucleotides which are not complementary to adjacent caspase-1-like protease nucleotides, can provide targeting specificity for caspase-1-like protease mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular caspase-1-like protease polynucleotide sequence.

Antisense oligonucleotides can be modified without affecting their ability to hybridize to an caspase-1-like protease polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., Trends Biotechnol. 10, 152–158, 1992; Uhlmann et al., Chem. Rev. 90, 543–584, 1990; Uhlmann et al., Tetrahedron. Lett. 215, 3539–3542, 1987.

Ribozymes

Ribozymes are RNA molecules with catalytic activity. See, e.g., Cech, Science 236, 1532–1539; 1987; Cech, Ann. Rev. Biochem. 59, 543–568; 1990, Cech, Curr. Opin. Struct. Biol. 2, 605–609; 1992, Couture & Stinchcomb, Trends Genet. 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of an caspase-1-like protease polynucleotide can be used to generate ribozymes which will specifically bind to mRNA transcribed from the caspase-1-like protease polynucleotide. Methods of designing and constructing ribozymes which can cleave other RNA molecules in trans in a highly sequence specific manner have been developed and described in the art (see Haseloff et al. Nature 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within an caspase-1-like protease RNA target are initially identified by scanning the RNA molecule for ribozyme cleavage sites which include the following sequences: GUA, GUU, and GUC. Once identified, short RNA sequences of between 15 and 20 ribonucleotides corresponding to the region of the caspase-1-like protease target RNA containing the cleavage site can be evaluated for secondary structural features which may render the target inoperable. The suitability of candidate targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related; thus, upon hybridizing to the caspase-1-like protease target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease caspase-1-like protease expression. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of caspase-1-like protease mRNA occurs only when both a ribozyme and a target gene are induced in the cells.

Screening Methods

The invention provides methods for identifying modulators, i.e., candidate or test compounds which bind to caspase-1-like protease polypeptides or polynucleotides and/or have a stimulatory or inhibitory effect on, for example, expression or activity of the caspase-1-like protease polypeptide or polynucleotide, so as to regulate degradation of the extracellular matrix. Decreased extracellular matrix degradation is useful for preventing or suppressing malignant cells from metastasizing. Increased extracellular matrix degradation may be desired, for example, in developmental disorders characterized by inappropriately low levels of extracellular matrix degradation or in regeneration.

The invention provides assays for screening test compounds which bind to or modulate the activity of an caspase-1-like protease polypeptide or an caspase-1-like protease polynucleotide. A test compound preferably binds to an caspase-1-like protease polypeptide or polynucleotide. More preferably, a test compound decreases an caspase-1-like protease activity of an caspase-1-like protease polypeptide or expression of an caspase-1-like protease polynucleotide by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. USA.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to caspase-1-like protease polypeptides or polynucleotides or to affect caspase-1-like protease activity or caspase-1-like protease gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies the active site or a fibronectin domain of the caspase-1-like protease polypeptide, thereby making the active site or fibronectin domain inaccessible to substrate such that normal biological activity is prevented. Examples of such small molecules include, but are not limited to, small peptides or peptide-like molecules. In binding assays, either the test compound or the caspase-1-like protease polypeptide can comprise a detectable label such as a fluorescent, radioisotopic, chemiluminescent, or enzymatic label, such as horseradish peroxidase, alkaline phosphatase, or luciferase. Detection of a test compound which is bound to the caspase-1-like protease polypeptide can then be accomplished, for example, by direct counting of radioemmission, by scintillation counting, or by determining conversion of an appropriate substrate to a detectable product.

Alternatively, binding of a test compound to an caspase-1-like protease polypeptide can be determined without labeling either of the interactants. For example, a microphysiometer can be used to detect binding of a test compound with a target polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and an caspase-1-like protease polypeptide. (McConnell et al., *Science* 257, 1906–1912, 1992).

Determining the ability of a test compound to bind to an caspase-1-like protease polypeptide also can be accomplished using a technology such as real-time Bimolecular Interaction Analysis (BIA). Sjolander & Urbaniczky, *Anal. Chem.* 63, 2338–2345, 1991, and Szabo et al., *Curr. Opin. Struct. Biol.* 5, 699–705, 1995. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an caspase-1-like protease polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the caspase-1-like protease polypeptide and modulate its activity.

The two-hybrid system is based on the modular nature of most transcription factors, which consist of separable DNA-binding and activation domains. Briefly, the assay utilizes two different DNA constructs. For example, in one construct a polynucleotide encoding an caspase-1-like protease polypeptide is fused to a polynucleotide encoding the DNA binding domain of a known transcription factor (e.g., GAL-4). In the other construct, a DNA sequence that encodes an unidentified protein ("prey" or "sample") is fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the caspase-1-like protease polypeptide.

It may be desirable to immobilize either the caspase-1-like protease polypeptide (or polynucleotide) or the test compound to facilitate separation of bound from unbound forms of one or both of the interactants, as well as to accommodate automation of the assay. Thus, either the caspase-1-like protease polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the caspase-1-like protease polypeptide (or polynucleotide) or test compound to a solid support, including use of covalent and non-covalent linkages, passive absorption, or pairs of binding moieties attached respectively to the polypeptide or test compound and the solid support. Test compounds are preferably bound to the solid support in an array, so that the location of individual test compounds can be tracked. Binding of a test compound to an caspase-1-like protease polypeptide (or polynucleotide) can be accomplished in any vessel suitable for containing the reactants. Examples of such vessels include microtiter plates, test tubes, and microcentrifuge tubes.

In one embodiment, an caspase-1-like protease polypeptide is a fusion protein comprising a domain that allows the caspase-1-like protease polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed caspase-1-like protease polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing polypeptides or polynucleotides on a solid support also can be used in the screening assays of the invention. For example, either an caspase-1-like protease polypeptide (or polynucleotide) or a test compound can be immobilized utilizing conjugation of biotin and streptavidin. Biotinylated caspase-1-like protease polypeptides or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an caspase-1-like protease polypeptide polynucleotides, or a test compound, but which do not interfere with a desired binding site, such as the active site or a fibronectin domain of the caspase-1-like protease polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the caspase-1-like protease polypeptide (or polynucleotides) or test compound, enzyme-linked assays which rely on detecting an caspase-1-like protease activity of the caspase-1-like protease polypeptide, and SDS gel electrophoresis under non-reducing conditions.

Screening for test compounds which bind to an caspase-1-like protease polypeptide or polynucleotide also can be carried out in an intact cell. Any cell which comprises an caspase-1-like protease polynucleotide or polypeptide can be used in a cell-based assay system. An caspase-1-like protease polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used. An intact cell is contacted with a test compound. Binding of the test compound to an caspase-1-like protease polypeptide or polynucleotide is determined as described above, after lysing the cell to release the caspase-1-like protease polypeptide-test compound complex.

Enzyme Assays

Test compounds can be tested for the ability to increase or decrease an caspase-1-like protease activity of an caspase-1-like protease polypeptide. Caspase-1-like protease activity can be measured, for example, using the method described in as described in Young et al., *J. Exp. Med* 191, 1535–44 (2000). Caspase-1-like protease activity can be measured after contacting either a purified caspase-1-like protease polypeptide, a cell extract, or an intact cell with a test compound. A test compound which decreases caspase-1-like protease activity by at least about 10, preferably about 50, more preferably about 75, 90, or 100% is identified as a potential therapeutic agent for decreasing extracellular matrix degradation. A test compound which increases caspase-1-like protease activity by at least about 10, preferably about 50, more preferably about 75, 90, or 100% is identified as a potential therapeutic agent for increasing extracellular matrix degradation.

Gene Expression

In another embodiment, test compounds which increase or decrease caspase-1-like protease gene expression are identified. An caspase-1-like protease polynucleotide is contacted with a test compound, and the expression of an RNA or polypeptide product of the caspase-1-like protease polynucleotide is determined. The level of expression of caspase-1-like protease mRNA or polypeptide in the presence of the test compound is compared to the level of expression of caspase-1-like protease mRNA or polypeptide in the absence of the test compound. The test compound can then be identified as a modulator of expression based on this comparison. For example, when expression of caspase-1-like protease mRNA or polypeptide is greater in the presence of the test compound than in its absence, the test compound is identified as a stimulator or enhancer of caspase-1-like protease mRNA or polypeptide is less expression. Alternatively, when expression of the mRNA or protein is less in the presence of the test compound than in its absence, the test compound is identified as an inhibitor of caspase-1-like protease mRNA or polypeptide expression.

The level of caspase-1-like protease mRNA or polypeptide expression in the cells can be determined by methods well known in the art for detecting mRNA or protein. Either qualitative or quantitative methods can be used. The presence of polypeptide products of an caspase-1-like protease polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into an caspase-1-like protease polypeptide.

Such screening can be carried out either in a cell-free assay system or in an intact cell. Any cell which expresses an caspase-1-like protease polynucleotide can be used in a cell-based assay system. The caspase-1-like protease polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used.

Pharmaceutical Compositions

The invention also provides pharmaceutical compositions which can be administered to a patient to achieve a therapeutic effect. Pharmaceutical compositions of the invention can comprise an caspase-1-like protease polypeptide, caspase-1-like protease polynucleotide, antibodies which specifically bind to an caspase-1-like protease polypeptide, or mimetics, agonists, antagonists, or inhibitors of an caspase-1-like protease polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMNGTON'S PHARMACEUTCAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Allergies and asthma . . . Allergy is a complex process in which enviromental antigens induce clinically adverse reactions. The inducing antigens, called allergens, typically elicit a specific IgE response and, although in most cases the allergens themselves have little or no intrinsic toxicity, they induce pathology when the IgE response in turn elicits an IgE-dependent or T cell-dependent hypersensitivity reaction. Hypersensitivity reactions can be local or systemic and typically occur within minutes of allergen exposure in individuals who have previously been sensitized to an allergen. The hypersensitivity reaction of allergy develops when the allergen is recognized by IgE antibodies bound to specific receptors on the surface of effector cells, such as mast cells, basophils, or eosinophils, which causes the activation of the effector cells and the release of mediators that produce the acute signs and symptoms of the reactions. Allergic diseases include asthma, allergic rhinitis (hay fever), atopic dermatitis, and anaphylaxis.

Asthma is though to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness caused by a decreased control of airway caliber, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to the tissue destruction related to the disorder. Other resident cells, such as smooth muscle cells, lung epithelial cells, mucus-producing cells, and nerve cells may also be abnormal in individuals with asthma and may contribute to the pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually make asthma a chronic disabling disorder requiring long-term management.

Despite recent important advances in our understanding of the pathophysiology of asthma, the disease appears to be increasing in prevalence and severity (Gergen and Weiss, Am Rev Respir Dis 146:823–824, 1992). It is estimated that 30–40% of the population suffer with atopic allergy, and 15% of children and 5% of adults in the population suffer from asthma (Gergen and Weiss, Am Rev Respir Dis 146: 823–824, 1992). Thus, an enormous burden is placed on our health care resources. However, both diagnosis and treatment of asthma are difficult. The severity of lung tissue inflammation is not easy to measure and the symptoms of the disease are often indistinguishable from those of respiratory infections, chronic respiratory inflammatory disorders, allergic rhinitis, or other respiratory disorders. Often, the inciting allergen cannot be determined, making removal of the causative environmental agent difficult. Current pharmacological treatments suffer their own set of disadvantages. Commonly used therapeutic agents, such as beta agonists, can act as symptom relievers to transiently improve pulmonary function, but do not affect the underlying inflammation. Agents that can reduce the underlying inflammation, such as anti-inflammatory steroids, can have major drawbacks that range from immunosuppression to bone loss (Goodman and Gilman's The Pharmacologic Basis of Therapeutics, Seventh Edition, MacMillan Publishing Company, NY, USA, 1985). In addition, many of the present therapies, such as inhaled corticosteroids, are short-lasting, inconvenient to use, and must be used often on a regular basis, in some cases for life, making failure of patients to comply with the treatment a major problem and thereby reducing their effectiveness as a treatment.

Because of the problems associated with conventional therapies, alternative treatment strategies have been evaluated. Glycophorin A (Chu and Sharom, Cell Immunol 145: 223–239, 1992), cyclosporin (Alexander et al., Lancet 1992, 339:324–328) and a nonapeptide fragment of IL-2 (Zav'yalov et al. Immunol Lett 1992, 31:285–288) all inhibit interleukin-2 dependent T lymphocyte proliferation; however, they are known to have many other effects. For example, cyclosporin is used as a immunosuppressant after organ transplantation. While these agents may represent alternatives to steroids in the treatment of asthmatics, they inhibit interleukin-2 dependent T lymphocyte proliferation and potentially critical immune functions associated with homeostasis. Other treatments that block the release or activity of mediators of bronchochonstriction, such as cromones or anti-leukotrienes, have recently been introduced for the treatment of mild asthma, but they are expensive and not effective in all patients and it is unclear whether they have any effect on the chronic changes associated with asthmatic inflammation. What is needed in the art is the identification of a treatment that can act in pathways critical to the development of asthma_that both blocks the episodic attacks of the disorder and preferentially dampens the hyperactive allergic immune response without immunocompromising the patient.

Cancer.

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Interleukin converting enzymes such as caspase-1 have been found to be involved in various types of leukemia; antagonists of human caspase-1-like protease therefore can be used to suppress leukemic cell proliferation.

The human caspase-1-like protease gene provides a therapeutic target for decreasing extracellular matrix degradation, in particular for treating or preventing metastatic cancer. For example, blocking a fibronectin domain of human ephrin-like serine protease can suppress or prevent migration or metastasis of tumor cells in response to fibronectin (9, 10). Cancers whose metastasis can be suppressed according to the invention include adenocarcinoma, melanoma, cancers of the adrenal gland, bladder, bone, breast, cervix, gall bladder, liver, lung, ovary, pancreas, prostate, testis, and uterus. Circulating tumor cells arrested in the capillary beds of different organs must invade the endothelial cell lining and degrade its underlying basement membrane (BM) in order to invade into the extravascular tissue(s) where they establish metastasis (1, 2). Metastatic tumor cells often attach at or near the intercellular junctions between adjacent endothelial cells. Such attachment of the metastatic cells is followed by rupture of the junctions, retraction of the endothelial cell borders and migration through the breach in the endothelium toward the exposed underlying BM (1, 11).

Once located between endothelial cells and the BM, the invading cells must degrade the sub endothelial glycoproteins and proteoglycans of the BM in order to migrate out of the vascular compartment. Several cellular enzymes (e.g. collagenase IV, plasminogen activator, cathepsin B, elastase) are thought to be involved in degradation of BM (2, 11). Suppression of human caspase-1-like protease activity therefore can be used to suppress tumor cell invasion and metastasis.

Human caspase-1 also can be regulated to treat neurodegenerative diseases, such as Alzheimer's disease.

The invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects caspase-1-like protease activity can be administered to a human cell, either in vitro or in vivo, to reduce caspase-1-like protease activity. The reagent preferably binds to an expression product of a human caspase-1-like protease gene. If the expression product is a polypeptide, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung or liver.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmol of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a tumor cell such as a tumor cell ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202-05 (1993); Chiou et al., GENE HERAPEUTICS: METHODS AND APPLICATIONS OF DIRECT GENE TRANSFER (J. A. Wolff, ed.) (1994); Wu & Wu, *J. Biol. Chem.* 263, 621-24 (1988); Wu et al., *J. Biol. Chem.* 269, 542-46 (1994); Zenke et al., *Proc. Natl. Acad. Sci. U.S.A.* 87, 3655-59 (1990); Wu et al., *J. Biol. Chem.* 266, 338-42 (1991).

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Determination of a Therapeutically Effective Dose

The determination of a therapeutically effective dose is well within the capability of those skilled in the art. A therapeutically effective dose refers to that amount of active ingredient which increases or decreases extracellular matrix degradation relative to that which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of an caspase-1-like protease polynucleotide or activity of an caspase-1-like protease polypeptide by at least about 10, preferably about 50, more preferably about 75, 90, or 100% relative to the absence of the reagent. The effectiveness of the mechanism chosen to decrease the level of expression of an caspase-1-like protease polynucleotide or the activity of an caspase-1-like protease polypeptide can be assessed using methods well known in the art, such as hybridization of nucleotide probes to caspase-1-like protease-specific mRNA, quantitative RT-PCR, immunologic detection of an caspase-1-like protease polypeptide, or measurement of caspase-1-like protease activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

The above disclosure generally describes the present invention, and all patents and patent applications cited in this disclosure are expressly incorporated herein. A more complete understanding can be obtained by reference to the following specific examples which are provided for purposes of illustration only and are not intended to limit the scope of the invention.

EXAMPLES

Example 1

Detection of Caspase-1-like Protease Activity

The polynucleotide of SEQ ID NO: 5 is inserted into the expression vector pCEV4 and the expression vector pCEV4-caspase-1-like protease polypeptide obtained is transfected into human embryonic kidney 293 cells. These cells are washed with PBS at 37° C. and resuspended in PBS at 4° C. Cells are harvested by centrifugation at 350×g for 10 min at 4° C. and treated with the fluorometric caspase assay system (Promega). Briefly, the cell pellet is resuspended in 10 µl hypotonic cell lysis buffer and centrifuged (16,000×g, 4° C., 20 min). The supernatant is preincubated for 30 min at 30° C. with 32 µl of the caspase assay buffer, 2 µl DMSO, 10 µl DTT (100 mM), and deionized water to a final volume of 100 µl. The samples are then incubated with 21 µl of the caspase-1 substrate Ac-YVAD-AMC (2.5 mM; AMC=7-amino-4-methylcoumarin) or the caspase-3 substrate Ac-DEVD-AMC (2.5 mM) for 1 h at 30° C. Fluorescence intensity is measured with the microplate reader. The specificity of the assay is verified by adding 2.5 mM of the caspase-1 inhibitor Ac-YVAD-CHO (D-CHO=aspart-1-al) or the caspase-3 inhibitor Ac-DEVD-CHO to the incubation mixture. It is shown that the polypeptide of SEQ ID NO: 6 has a caspase-1-like protease activity.

Example 2

Expression of Recombinant Caspase-1-like Protease

The *Pichia pastoris* expression vector pPICZB (Invitrogen, San Diego, Calif.) is used to produce large quantities of a recombinant human caspase-1-like protease in yeast. The encoding DNA sequence is derived from the nucleotide sequence shown in SEQ ID NO:5. Before insertion into vector pPICZB, the DNA sequence is modified by well known methods in such a way that it contains at its 5'-end an initiation codon and at its 3'-end an enterokinase cleavage site, a His6 reporter tag, and a termination codon. Moreover, at both termini recognition sequences for restriction endonucleases are added.

After digestion of the multiple cloning site of pPICZ B with the corresponding restriciton enzymes, the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks, and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human caspase-1-like protease is obtained.

Example 3

Identification of a Test Compound which Binds to an Caspase-1-like Protease Polypeptide Purified caspase-1-like protease polypeptides comprising a glutathione-S-transferase protein and absorbed onto glutathione-derivatized wells of 96-well microtiter plates are contacted with test compounds from a small molecule library at pH 7.0 in a physiological buffer solution. Caspase-1-like protease polypeptides comprise the amino acid sequence shown in SEQ ID NO:2 or 6. The test compounds comprise a fluorescent tag. The samples are incubated for 5 minutes to one hour. Control samples are incubated in the absence of a test compound.

The buffer solution containing the test compounds is washed from the wells. Binding of a test compound to an caspase-1-like protease polypeptide is detected by fluorescence measurements of the contents of the wells. A test compound which increases the fluorescence in a well by at least 15% relative to fluorescence of a well in which a test compound was not incubated is identified as a compound which binds to an caspase-1-like protease polypeptide.

Example 4

Identification of a Test Compound which Decreases Caspase-1-like Protease Activity Cellular extracts from the human colon cancer cell line HCT116 are contacted with test compounds from a small molecule library and assayed for caspase-1-like protease activity. Control extracts, in the absence of a test compound, also are assayed. Aspartyl protease activity can be measured as described in as described in Young et al., *J. Exp. Med.* 191, 1535–44 (2000).

A test compound which decreases caspase-1-like protease activity of the extract relative to the control extract by at least 20% is identified as an caspase-1-like protease inhibitor.

Example 5

Identification of a Test Compound which Decreases Caspase-1-like Protease Gene Expression A test compound is administered to a culture of the breast tumor cell line MDA-468 and incubated at 37° C. for 10 to 45 minutes. A culture of the same type of cells incubated for the same time without the test compound provides a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled caspase-1-like protease-specific probe at 65° C. in Express-hyb (CLONTECH). The probe comprises at least 11 contiguous nucleotides selected from SEQ ID NO:1 or 5. A test compound which decreases the caspase-1-like protease-specific signal relative to the signal obtained in the absence of the test compound is identified as an inhibitor of caspase-1-like protease gene expression.

Example 6

Treatment of Leukemia with a Reagent which Specifically Binds to an Caspase-1-like Protease Gene Product Synthesis of antisense caspase-1-like protease oligonucleotides comprising at least 11 contiguous nucleotides selected from SEQ ID NO:1 or 5 is performed on a Pharmacia Gene Assembler series synthesizer using the phosphoramidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the *Limulus* Amebocyte Assay (Bang, *Biol. Bull.* (*Woods Hole, Mass.*) 105, 361–362, 1953).

An aqueous composition containing the antisense oligonucleotides at a concentration of 0.1–100 μM is administered to a patient with leukemia. The patient is monitored over a period of days or weeks. Additional injections of the antisense oligonucleotides can be given during that time. The patient's leukemia is treated due to decreased caspase-1-like protease activity.

Example 7

Expression Profiling of Caspase-1-like Protease

Quantitative RT-PCR analysis of RNA from different human tissues was performed to investigate the tissue distribution of caspase-1-like protease mRNA. In most cases, 25 μg of total RNA from various tissues (including Human Total RNA Panel I-V, Clontech Laboratories, Palo Alto, Calif., USA) was used as a template to synthesize first-strand cDNA using the SUPERSCRIPT™ First-Strand Synthesis System for RT-PCR (Life Technologies, Rockville, Md., USA). First-strand cDNA synthesis was carried out according to the manufacturer's protocol using oligo (dT) to hybridize to the 3' poly A tails of mRNA and prime the synthesis reaction. 10 ng of the first-strand cDNA was then used as template in a polymerase chain reaction. In other cases, 10 ng of commercially available cDNAs (Human Immune System MTC Panel and Human Blood Fractions MTC Panel, Clontech Laboratories, Palo Alto, Calif., USA) were used as template in a polymerase chain reaction. The polymerase chain reaction was performed in a LightCycler (Roche Molecular Biochemicals, Indianapolis, Ind., USA), in the presence of the DNA-binding fluorescent dye SYBR Green I which binds to the minor groove of the DNA double helix, produced only when double-stranded DNA is successfully synthesized in the reaction (Morrison et al., 1998). Upon binding to double-stranded DNA, SYBR Green I emits light that can be quantitatively measured by the LightCycler machine. The polymerase chain reaction was carried out using the gene specific oligonucleotide primers LBRI 116-L1 and LBRI116-R1 and measurements of the intensity of emitted light were taken following each cycle of the reaction when the reaction had reached a temperature of 91 degrees C. Intensities of emitted light were converted into copy numbers of the gene transcript per nanogram of template cDNA by comparison with simultaneously reacted standards of known concentration.

Results are given in FIG. 8. Human caspase-1-like protease of the present invention is specifically expressed in lung and spleen. The human caspase-1-like protease of the present invention therefore represents a drug target that can be utilized to modulate immune-related and/or respiratory diseases.

Example 8

Expression Profiling of Caspase-1-like Protease in Immune and Airway System

Quantitative RT-PCR analysis of RNA from different human tissues was performed to investigate the cell distribution of caspase-1-like protease mRNA in immune and airway system. In most cases, 25 μg of total RNA from various tissues (including Human Total RNA Panel I-V, Clontech Laboratories, Palo Alto, Calif., USA) was used as a template to synthesize first-strand cDNA using the SUPERSCRIPT™ First-Strand Synthesis System for RT-PCR (Life Technologies, Rockville, Md., USA). First-strand cDNA synthesis was carried out according to the manufacturer's protocol using oligo (dT) to hybridize to the 3' poly A tails of mRNA and prime the synthesis reaction. 10 ng of the first-strand cDNA was then used as template in a polymerase chain reaction. In other cases, 10 ng of commercially available cDNAs (Human Immune System MTC Panel and Human Blood Fractions MTC Panel, Clontech Laboratories, Palo Alto, Calif., USA) were used as template in a polymerase chain reaction. The polymerase chain reaction was performed in a LightCycler (Roche Molecular Biochemicals, Indianapolis, Ind., USA), in the presence of the DNA-binding fluorescent dye SYBR Green I which binds to the minor groove of the DNA double helix, produced only when double-stranded DNA is successfully synthesized in the reaction (Morrison et al., 1998). Upon binding to double-stranded DNA, SYBR Green I emits light that can be quantitatively measured by the LightCycler machine. The polymerase chain reaction was carried out using the gene specific oligonucleotide primers LBRI 116-L2 and LBRI116-R1 and measurements of the intensity of emitted light were taken following each cycle of the reaction when the reaction had reached a temperature of 91° C. Intensities of emitted light were converted into copy numbers of the gene transcript per nanogram of template cDNA by comparison with simultaneously reacted standards of known concentration.

Results are given in FIG. 9.

REFERENCES

1. Nicolson (1988) Organ specificity of tumor metastasis: Role of preferential adhesion, invasion and growth of malignant cells at specific secondary sites. *Cancer Met. Rev.* 7, 143–188.
2. Liotta et al. (1983) Tumor invasion and the extracellular matrix. *Lab. Invest.* 49, 639–649.
3. Vlodavsky et al. (1987) Endothelial cell-derived basic fibroblast growth factor: Synthesis and deposition into sub endothelial extracellular matrix. *Proc. Natl. Acad. Sci. USA* 84, 2292–2296.
4. Folkman et al. (1980) A heparin-binding angiogenic protein—basic fibroblast growth factor—is stored within basement membrane. *Am. J. Pathol.* 130, 393400.
5. Cardon-Cardo et al. (1990) Expression of basic fibroblast growth factor in normal human tissues. *Lab. Invest.* 63, 832–840.
6. Vlodavsky et al. (1991) Extracellular sequestration and release of fibroblast growth factor: a regulatory mechanism? *Trends Biochem. Sci.* 16, 268–271.
7. Vlodavsky et al. (1993) Extracellular matrix-bound growth factors, enzymes and plasma proteins. In BASEMENT MEMBRANES: CELLULAR AND MOLECULAR ASPECTS Rohrbach & Timpl, eds., pp 327–343. Academic Press Inc., Orlando, Fla.
8. Ross (1993) The pathogenesis of atherosclerosis: a perspective for the 1990s. *Nature (Lond.).* 362, 801–809.
9. McCarthy et al. (1986). Human fibronectin contains distinct adhesion- and motility-promoting domains for metastatic melanoma cells. *J. Cell Biol.* 102, 179–88.
10. Van Muijen et al. (1995) Properties of metastasizing and non-metastasizing human melanoma cells. *Recent Results in Cancer Research* 139, 104–22.
11. Price et al. (1997) The Biochemistry of Cancer Dissemination, in *Critical Reviews in Biochemistry and Mol. Biol.* 32, 175–253.
12. Leytus S P, Loeb K R, Hagen F S, Kurachi K, Davie E W. A novel trypsin-like serine protease (hepsin) with a putative epidermis-specific domain expressed by human liver and hepatoma cells. Biochemistry. 1988 Feb. 9;27(3):1067–74.
13. Tanimoto H, Yan Y, Clarke J, Korourian S, Shigemasa K, Parmley T H, Parham G P, O'Brien T J. Hepsin, a cell surface serine protease identified in hepatoma cells, is overexpressed in ovarian cancer. Cancer Res. 1997 Jul. 15;57(14):2884–7.
14. Zacharski L R, Omstein D L, Memoli V A, Rousseau S M, Kisiel W. Expression of the factor VII activating protease, hepsin, in situ in renal cell carcinoma Thromb Haemost. 1998 April; 79(4):876–7.

The invention claimed is:

1. A method of screening for candidate therapeutic agents, comprising the steps of:

contacting a protein comprising the amino acid sequence shown in SEQ ID NO:6 with a test compound;

assaying for binding between the protein and the test compound; and identifying a test compound that binds to the protein as a candidate therapeutic agent that may be useful for regulating activity of the protein.

2. The method of claim 1 wherein either the test compound or the protein comprises a detectable label.

3. The method of claim 1 wherein either the test compound or the protein is bound to a solid support.

* * * * *

SEQUENCE LISTING

<160> NUMBER OF SEQ ID NOS: 6

<210> SEQ ID NO 1
<211> LENGTH: 431
<212> TYPE: DNA
<213> ORGANISM: Homo sapiens

<400> SEQUENCE: 1

```
tttttttttt tttgaaagga aactgggtag ttctttattg taaagggcag aaacgtgcaa      60
ttacagattg tgaaactgct gcttagaatt ccaggctcat tgtaaggaag tgccttgtcg     120
tcagcaagtt gacatccaag tactggaact tagtttcttc cggccctcag acattcatac     180
agcttcctta ttttaatgta ctgggaagag atagaaacgt cttgtcgaag taactctttc     240
agtgctgggc atctgtgctt tatcatctgg ctgctcaaat gaaagttgaa cctaatgtgg     300
aagagcagaa agcaataaaa tccttctcta tgtgtacttg attaatagca tcatcctcaa     360
aatctcccgg agttggtaaa gatatatttt cagaggccgg tactgaatct tttaccaaca     420
ccacaccatg g                                                          431
```

<210> SEQ ID NO 2
<211> LENGTH: 79
<212> TYPE: PRT
<213> ORGANISM: Homo sapiens

<400> SEQUENCE: 2

```
His Gly Val Val Leu Val Lys Asp Ser Val Pro Ala Ser Glu Asn Ile
  1               5                  10                  15

Ser Leu Pro Thr Pro Gly Asp Phe Glu Asp Asp Ala Ile Asn Gln Val
             20                  25                  30
```

-continued

```
His Ile Glu Lys Asp Phe Ile Ala Phe Cys Ser Ser Thr Leu Gly Val
            35                  40                  45

Gln Leu Ser Phe Glu Gln Pro Asp Lys Ala Gln Met Pro Ser Thr
 50                  55                  60

Glu Arg Val Thr Ser Thr Arg Arg Phe Tyr Leu Phe Pro Val His
 65                  70                  75
```

<210> SEQ ID NO 3
<211> LENGTH: 363
<212> TYPE: DNA
<213> ORGANISM: Homo sapiens

<400> SEQUENCE: 3

| | | | | | |
|---|---|---|---|---|---|
| ttttttttttt | tgaaaggaaa | ctgtgtattt | ctttattgta | aagggcagaa | acgtgcaatt | 60 |
| acagattgtg | aaactgctgc | ttagaattcc | aggctcattg | taaggaagtg | ccttgtcgtc | 120 |
| agcaagttga | catccaagta | ctggaactta | gtttcttccg | gccctcagac | attcatacag | 180 |
| cttccttatt | ttaatgtact | gggaagagat | agaaacgtct | tgtcgaagta | actctttcag | 240 |
| tgctgggcat | ctgtgcttta | tcatctggct | gctcaaatga | agttgaacc | taatgtggaa | 300 |
| gagcagaaag | caataaaatc | cttctctatg | tgtacttgat | taatagcatc | atcctcaaaa | 360 |
| tct | | | | | | 363 |

<210> SEQ ID NO 4
<211> LENGTH: 404
<212> TYPE: PRT
<213> ORGANISM: Homo sapiens

<400> SEQUENCE: 4

```
Met Ala Asp Lys Val Leu Lys Glu Lys Arg Lys Leu Phe Ile Arg Ser
  1               5                  10                  15

Met Gly Glu Gly Thr Ile Asn Gly Leu Leu Asp Glu Leu Leu Gln Thr
             20                  25                  30

Arg Val Leu Asn Lys Glu Glu Met Glu Lys Val Lys Arg Glu Asn Ala
         35                  40                  45

Thr Val Met Asp Lys Thr Arg Ala Leu Ile Asp Ser Val Ile Pro Lys
 50                  55                  60

Gly Ala Gln Ala Cys Gln Ile Cys Ile Thr Tyr Ile Cys Glu Glu Asp
 65                  70                  75                  80

Ser Tyr Leu Ala Gly Thr Leu Gly Leu Ser Ala Asp Gln Thr Ser Gly
             85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
            115                 120                 125

Ser Glu Gly Asn Val Lys Leu Cys Ser Leu Glu Glu Ala Gln Arg Ile
        130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205
```

```
Ser Asp Met Thr Thr Glu Leu Glu Ala Phe Ala His Arg Pro Glu His
    210                 215                 220
Lys Thr Ser Asp Ser Thr Phe Leu Val Phe Met Ser His Gly Ile Arg
225                 230                 235                 240
Glu Gly Ile Cys Gly Lys Lys His Ser Glu Gln Val Pro Asp Ile Leu
                245                 250                 255
Gln Leu Asn Ala Ile Phe Asn Met Leu Asn Thr Lys Asn Cys Pro Ser
            260                 265                 270
Leu Lys Asp Lys Pro Lys Val Ile Ile Gln Ala Cys Arg Gly Asp
        275                 280                 285
Ser Pro Gly Val Val Trp Phe Lys Asp Ser Val Gly Val Ser Gly Asn
    290                 295                 300
Leu Ser Leu Pro Thr Thr Glu Glu Phe Glu Asp Asp Ala Ile Lys Lys
305                 310                 315                 320
Ala His Ile Glu Lys Asp Phe Ile Ala Phe Cys Ser Ser Thr Pro Asp
                325                 330                 335
Asn Val Ser Trp Arg His Pro Thr Met Gly Ser Val Phe Ile Gly Arg
            340                 345                 350
Leu Ile Glu His Met Gln Glu Tyr Ala Cys Ser Cys Asp Val Glu Glu
        355                 360                 365
Ile Phe Arg Lys Val Arg Phe Ser Phe Glu Gln Pro Asp Gly Arg Ala
    370                 375                 380
Gln Met Pro Thr Thr Glu Arg Val Thr Leu Thr Arg Cys Phe Tyr Leu
385                 390                 395                 400
Phe Pro Gly His

<210> SEQ ID NO 5
<211> LENGTH: 1252
<212> TYPE: DNA
<213> ORGANISM: Homo sapiens
<220> FEATURE:
<221> NAME/KEY: misc_feature
<222> LOCATION: (1)...(1252)
<223> OTHER INFORMATION: n = A,T,C or G

<400> SEQUENCE: 5
acacaagaag ggaggagaga aaagccatgg ccgnnnacaa ggtcctgaag gagaagagaa      60
agcagtttat ccgttcagtg ggcgaaggta caataaatgg cttactgggt gaattattgg     120
agacaagggt gctgagccag gaagagatag agatagtaaa atgtgaaaat gctacagtta     180
tggataaggc ccgagctttg cttgactctg ttattcggaa aggggctcca gcatgccaaa     240
tttgcatcac atacatttgt gaagaagaca gtcacctggc agggacgctg ggactctcag     300
cagnnngtcc aacatctgga aatcacctta ctacacaaga ttctcaaata gtacttcctt     360
ccactcctca ggctgtggca gtgtgggaca gccctgctat gcctacatcc tcaggctcag     420
gaggaagcat caagctttgc tccctagacg aagctaaaag gatatggaaa gaaagttga     480 cagagnnnnn nnnnatttat ccaataatgg gcaagtcaag ctgcacacat cnnnttgctc     540
tcattatctt taacaaagag tttgacagtc tttctaaaag agtgggagct gaggttgatg     600
tcataggcat gatgatgctg ctacaaaatc tggggtacaa ggtggatgag aaaagaaatc     660
tcactgcttc ggaaatgact acagagttgg aagtattttc tctgcaccaa gagcacaagg     720
cctcttctca tggtattcgg gaaggcattt gtgggaagaa atactctgag caagtcccag     780
atgtattaca actcaatgaa atctttaaaa cgttgaatag caagaactgc ccaagtttga     840
aggacaaacc caaggtgata atcatccagg cctgccatcc agagaaccat ggtgtggtgt     900
```

-continued

```
tggtaaaaga ttcagtaccg gcctctgaaa atatatcttt accaactccg ggagattttg    960
aggatgatgc tattaatcaa gtacacatag agaaggattt tattgctttc tgctcttcca   1020
caatagataa tgtttgctgg agacatcctg caaagggctc tgtcattgaa caactgcaag   1080
aatattcctg ttcctgtgat gtggaggaaa ttttccacaa gatagggctc tcatttgagc   1140
agccagatga taaagcacag atgcccagca ctgaaagagt tacttcgaca agacgtttct   1200
atctcttccc agtacattaa aataaggaag ctgtatgaat gtctgagggc cg           1252
```

<210> SEQ ID NO 6
<211> LENGTH: 397
<212> TYPE: PRT
<213> ORGANISM: Homo sapiens
<220> FEATURE:
<221> NAME/KEY: VARIANT
<222> LOCATION: (1)...(397)
<223> OTHER INFORMATION: Xaa = Any Amino Acid

<400> SEQUENCE: 6

```
Met Ala Xaa Xaa Lys Val Leu Lys Glu Lys Arg Lys Gln Phe Ile Arg
 1               5                  10                  15

Ser Val Gly Glu Gly Thr Ile Asn Gly Leu Leu Gly Glu Leu Leu Glu
            20                  25                  30

Thr Arg Val Leu Ser Gln Glu Glu Ile Glu Ile Val Lys Cys Glu Asn
        35                  40                  45

Ala Thr Val Met Asp Lys Ala Arg Ala Leu Leu Asp Ser Val Ile Arg
    50                  55                  60

Lys Gly Ala Pro Ala Cys Gln Ile Cys Ile Thr Tyr Ile Cys Glu Glu
65                  70                  75                  80

Asp Ser His Leu Ala Gly Thr Leu Gly Leu Ser Ala Xaa Xaa Pro Thr
                85                  90                  95

Ser Gly Asn His Leu Thr Thr Gln Asp Ser Gln Ile Val Leu Pro Ser
            100                 105                 110

Thr Pro Gln Ala Val Ala Val Trp Asp Ser Pro Ala Met Pro Thr Ser
        115                 120                 125

Ser Gly Ser Gly Gly Ser Ile Lys Leu Cys Ser Leu Asp Glu Ala Lys
    130                 135                 140

Arg Ile Trp Lys Glu Lys Leu Thr Glu Xaa Xaa Xaa Ile Tyr Pro Ile
145                 150                 155                 160

Met Gly Lys Ser Ser Cys Thr His Xaa Xaa Ala Leu Ile Ile Phe Asn
                165                 170                 175

Lys Glu Phe Asp Ser Leu Ser Lys Arg Val Gly Ala Glu Val Asp Val
            180                 185                 190

Ile Gly Met Met Met Leu Leu Gln Asn Leu Gly Tyr Lys Val Asp Glu
        195                 200                 205

Lys Arg Asn Leu Thr Ala Ser Glu Met Thr Thr Glu Leu Glu Val Phe
    210                 215                 220

Ser Leu His Gln Glu His Lys Ala Ser His Gly Ile Arg Glu Gly
225                 230                 235                 240

Ile Cys Gly Lys Lys Tyr Ser Glu Gln Val Pro Asp Val Leu Gln Leu
                245                 250                 255

Asn Glu Ile Phe Lys Thr Leu Asn Ser Lys Asn Cys Pro Ser Leu Lys
            260                 265                 270

Asp Lys Pro Lys Val Ile Ile Gln Ala Cys His Pro Glu Asn His
        275                 280                 285
```

-continued

```
Gly Val Val Leu Val Lys Asp Ser Val Pro Ala Ser Glu Asn Ile Ser
        290                 295                 300

Leu Pro Thr Pro Gly Asp Phe Glu Asp Asp Ala Ile Asn Gln Val His
305                 310                 315                 320

Ile Glu Lys Asp Phe Ile Ala Phe Cys Ser Ser Thr Ile Asp Asn Val
                325                 330                 335

Cys Trp Arg His Pro Ala Lys Gly Ser Val Ile Glu Gln Leu Gln Glu
            340                 345                 350

Tyr Ser Cys Ser Cys Asp Val Glu Glu Ile Phe His Lys Ile Gly Leu
        355                 360                 365

Ser Phe Glu Gln Pro Asp Asp Lys Ala Gln Met Pro Ser Thr Glu Arg
        370                 375                 380

Val Thr Ser Thr Arg Arg Phe Tyr Leu Phe Pro Val His
385                 390                 395
```